(12) United States Patent
Bonhoeffer et al.

(10) Patent No.: US 8,961,593 B2
(45) Date of Patent: Feb. 24, 2015

(54) PROSTHETIC HEART VALVE SYSTEMS

(71) Applicant: Medtronic, Inc., Minneapolis, MN (US)

(72) Inventors: Philipp Bonhoeffer, London (GB); Timothy R. Ryan, Shorewood, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 14/097,608

(22) Filed: Dec. 5, 2013

(65) Prior Publication Data
US 2014/0094905 A1 Apr. 3, 2014

Related U.S. Application Data

(60) Division of application No. 13/178,112, filed on Jul. 7, 2011, now Pat. No. 8,613,765, which is a continuation of application No. 12/380,483, filed on Feb. 27, 2009, now abandoned.

(60) Provisional application No. 61/032,185, filed on Feb. 28, 2008.

(51) Int. Cl.
*A61F 2/24* (2006.01)

(52) U.S. Cl.
CPC ............. *A61F 2/2412* (2013.01); *A61F 2/2418* (2013.01); *A61F 2250/0082* (2013.01); *A61F 2220/0075* (2013.01); *A61F 2230/0078* (2013.01)
USPC ........................... 623/2.1; 623/1.26; 623/2.12

(58) Field of Classification Search
CPC ..................................... A61F 2/06; A61F 2/07
USPC ............. 623/1.13, 1.15, 1.24, 1.26, 1.3, 1.31, 623/2.1–2.19
See application file for complete search history.

(56) References Cited

U.S. PATENT DOCUMENTS

| | | | |
|---|---|---|---|
| 3,334,629 | A | 8/1967 | Cohn |
| 3,409,013 | A | 11/1968 | Berry |
| 3,657,744 | A | 4/1972 | Ersek |
| 3,671,979 | A | 6/1972 | Moulopoulos |
| 3,714,671 | A | 2/1973 | Edwards et al. |
| 3,755,823 | A | 9/1973 | Hancock |
| 3,868,956 | A | 3/1975 | Alfidi et al. |

(Continued)

FOREIGN PATENT DOCUMENTS

| | | |
|---|---|---|
| DE | 195 32 846 | 3/1997 |
| DE | 195 46 692 A1 | 6/1997 |

(Continued)

OTHER PUBLICATIONS

U.S. Appl. No. 12/250,163, filed Oct. 13, 2008.
U.S. Appl. No. 61/192,199, filed Sep. 15, 2008.
U.S. Appl. No. 12/253,858, filed Oct. 17, 2008.
U.S. Appl. No. 12/596,343, filed Apr. 14, 2008.
U.S. Appl. No. 61/129,170, filed Jun. 9, 2008.

(Continued)

*Primary Examiner* — Jason-Dennis Stewart

(57) ABSTRACT

A heart valve that can be expanded following its implantation in a patient, such as to accommodate the growth of a patient and the corresponding growth of the area where the valve is implanted, and to minimize paravalvular leakage. In one aspect, the invention may maximize the orifice size of the surgical valve. The invention includes expandable implantable conduits and expandable bioprosthetic stented valves. In one aspect of the invention, the valve may be adapted to accommodate growth of a patient to address limitation on bioprosthetic valve lifespans.

13 Claims, 5 Drawing Sheets

(56) References Cited

U.S. PATENT DOCUMENTS

| | | |
|---|---|---|
| 4,035,849 A | 7/1977 | Angell et al. |
| 4,056,854 A | 11/1977 | Boretos et al. |
| 4,106,129 A | 8/1978 | Carpentier et al. |
| 4,222,126 A | 9/1980 | Boretos et al. |
| 4,233,690 A | 11/1980 | Akins |
| 4,265,694 A | 5/1981 | Boretos |
| 4,297,749 A | 11/1981 | Davis et al. |
| 4,470,157 A | 9/1984 | Love |
| 4,501,030 A | 2/1985 | Lane |
| 4,574,803 A | 3/1986 | Storz |
| 4,580,568 A | 4/1986 | Gianturco |
| 4,592,340 A | 6/1986 | Boyles |
| 4,610,688 A | 9/1986 | Silvestrini et al. |
| 4,612,011 A | 9/1986 | Kautzky |
| 4,647,283 A | 3/1987 | Carpentier et al. |
| 4,648,881 A | 3/1987 | Carpentier et al. |
| 4,662,885 A | 5/1987 | DiPisa, Jr. |
| 4,665,906 A | 5/1987 | Jervis |
| 4,681,908 A | 7/1987 | Broderick et al. |
| 4,710,192 A | 12/1987 | Liotta et al. |
| 4,733,665 A | 3/1988 | Palmaz |
| 4,777,951 A | 10/1988 | Cribier et al. |
| 4,787,899 A | 11/1988 | Lazarus |
| 4,787,901 A | 11/1988 | Baykut |
| 4,796,629 A | 1/1989 | Grayzel |
| 4,819,751 A | 4/1989 | Shimada et al. |
| 4,834,755 A | 5/1989 | Silvestrini et al. |
| 4,856,516 A | 8/1989 | Hillstead |
| 4,872,874 A | 10/1989 | Taheri |
| 4,878,495 A | 11/1989 | Grayzel |
| 4,878,906 A | 11/1989 | Lindemann et al. |
| 4,883,458 A | 11/1989 | Shiber |
| 4,909,252 A | 3/1990 | Goldberger |
| 4,917,102 A | 4/1990 | Miller et al. |
| 4,922,905 A | 5/1990 | Strecker |
| 4,954,126 A | 9/1990 | Wallsten |
| 4,966,604 A | 10/1990 | Reiss |
| 4,979,939 A | 12/1990 | Shiber |
| 4,986,830 A | 1/1991 | Owens et al. |
| 4,994,077 A | 2/1991 | Dobben |
| 5,007,896 A | 4/1991 | Shiber |
| 5,026,366 A | 6/1991 | Leckrone |
| 5,032,128 A | 7/1991 | Alonso |
| 5,037,434 A | 8/1991 | Lane |
| 5,047,041 A | 9/1991 | Samuels |
| 5,059,177 A | 10/1991 | Towne et al. |
| 5,085,635 A | 2/1992 | Cragg |
| 5,089,015 A | 2/1992 | Ross |
| 5,152,771 A | 10/1992 | Sabbaghian et al. |
| 5,161,547 A | 11/1992 | Tower |
| 5,163,953 A | 11/1992 | Vince |
| 5,167,628 A | 12/1992 | Boyles |
| 5,217,483 A | 6/1993 | Tower |
| 5,232,445 A | 8/1993 | Bonzel |
| 5,272,909 A | 12/1993 | Nguyen et al. |
| 5,295,958 A | 3/1994 | Shturman |
| 5,327,774 A | 7/1994 | Nguyen et al. |
| 5,332,402 A | 7/1994 | Teitelbaum et al. |
| 5,350,398 A | 9/1994 | Pavcnik et al. |
| 5,370,685 A | 12/1994 | Stevens |
| 5,397,351 A | 3/1995 | Pavcnik et al. |
| 5,411,552 A | 5/1995 | Andersen et al. |
| 5,415,633 A | 5/1995 | Lazarus et al. |
| 5,431,676 A | 7/1995 | Dubrul et al. |
| 5,443,446 A | 8/1995 | Shturman |
| 5,480,424 A | 1/1996 | Cox |
| 5,489,294 A | 2/1996 | McVenes et al. |
| 5,489,297 A | 2/1996 | Duran |
| 5,496,346 A | 3/1996 | Horzewski et al. |
| 5,500,014 A | 3/1996 | Quijano et al. |
| 5,507,767 A | 4/1996 | Maeda et al. |
| 5,545,209 A | 8/1996 | Roberts et al. |
| 5,545,211 A | 8/1996 | An et al. |
| 5,545,214 A | 8/1996 | Stevens |
| 5,554,185 A | 9/1996 | Block et al. |
| 5,575,818 A | 11/1996 | Pinchuk |
| 5,580,922 A | 12/1996 | Park et al. |
| 5,591,195 A | 1/1997 | Taheri et al. |
| 5,609,626 A | 3/1997 | Quijano et al. |
| 5,645,559 A | 7/1997 | Hachtman et al. |
| 5,665,115 A | 9/1997 | Cragg |
| 5,667,523 A | 9/1997 | Bynon et al. |
| 5,674,277 A | 10/1997 | Freitag |
| 5,702,368 A | 12/1997 | Stevens et al. |
| 5,713,953 A | 2/1998 | Vallana et al. |
| 5,716,417 A | 2/1998 | Girard et al. |
| 5,746,709 A | 5/1998 | Rom et al. |
| 5,749,890 A | 5/1998 | Shaknovich |
| 5,766,151 A | 6/1998 | Valley et al. |
| 5,782,809 A | 7/1998 | Umeno et al. |
| 5,800,456 A | 9/1998 | Maeda et al. |
| 5,800,508 A | 9/1998 | Goicoechea et al. |
| 5,817,126 A | 10/1998 | Imran |
| 5,824,041 A | 10/1998 | Lenker |
| 5,824,043 A | 10/1998 | Cottone, Jr. |
| 5,824,053 A | 10/1998 | Khosravi et al. |
| 5,824,056 A | 10/1998 | Rosenberg |
| 5,824,061 A | 10/1998 | Quijano et al. |
| 5,824,064 A | 10/1998 | Taheri |
| 5,840,081 A | 11/1998 | Andersen et al. |
| 5,843,158 A | 12/1998 | Lenker et al. |
| 5,851,232 A | 12/1998 | Lois |
| 5,855,597 A | 1/1999 | Jayaraman |
| 5,855,601 A | 1/1999 | Bessler et al. |
| 5,861,028 A | 1/1999 | Angell |
| 5,876,448 A | 3/1999 | Thompson et al. |
| 5,888,201 A | 3/1999 | Stinson et al. |
| 5,891,191 A | 4/1999 | Stinson |
| 5,906,619 A | 5/1999 | Olson et al. |
| 5,913,842 A | 6/1999 | Boyd et al. |
| 5,925,063 A | 7/1999 | Khosravi |
| 5,944,738 A | 8/1999 | Amplatz et al. |
| 5,954,766 A | 9/1999 | Zadno-Azizi et al. |
| 5,957,949 A | 9/1999 | Leonhardt et al. |
| 5,968,068 A | 10/1999 | Dehdashtian et al. |
| 5,984,957 A | 11/1999 | Laptewicz, Jr. et al. |
| 5,997,573 A | 12/1999 | Quijano et al. |
| 6,022,370 A | 2/2000 | Tower |
| 6,027,525 A | 2/2000 | Suh et al. |
| 6,029,671 A | 2/2000 | Stevens et al. |
| 6,042,589 A | 3/2000 | Marianne |
| 6,042,598 A | 3/2000 | Tsugita et al. |
| 6,042,607 A | 3/2000 | Williamson, IV |
| 6,051,014 A | 4/2000 | Jang |
| 6,059,809 A | 5/2000 | Amor et al. |
| 6,110,201 A | 8/2000 | Quijano et al. |
| 6,146,366 A | 11/2000 | Schachar |
| 6,159,239 A | 12/2000 | Greenhalgh |
| 6,162,208 A | 12/2000 | Hipps |
| 6,162,245 A | 12/2000 | Jayaraman |
| 6,171,335 B1 | 1/2001 | Wheatley et al. |
| 6,200,336 B1 | 3/2001 | Pavcnik et al. |
| 6,203,550 B1 | 3/2001 | Olson |
| 6,210,408 B1 | 4/2001 | Chandrasekaran et al. |
| 6,218,662 B1 | 4/2001 | Tchakarov et al. |
| 6,221,006 B1 | 4/2001 | Dubrul et al. |
| 6,221,091 B1 | 4/2001 | Khosravi |
| 6,241,757 B1 | 6/2001 | An et al. |
| 6,245,102 B1 | 6/2001 | Jayaraman |
| 6,248,116 B1 | 6/2001 | Chevilon |
| 6,258,114 B1 | 7/2001 | Konya et al. |
| 6,258,115 B1 | 7/2001 | Dubrul |
| 6,258,120 B1 | 7/2001 | McKenzie et al. |
| 6,277,555 B1 | 8/2001 | Duran et al. |
| 6,299,637 B1 | 10/2001 | Shaolia et al. |
| 6,302,906 B1 | 10/2001 | Goicoechea et al. |
| 6,309,382 B1 | 10/2001 | Garrison et al. |
| 6,309,417 B1 | 10/2001 | Spence et al. |
| 6,338,735 B1 | 1/2002 | Stevens |
| 6,348,063 B1 | 2/2002 | Yassour et al. |
| 6,350,277 B1 | 2/2002 | Kocur |
| 6,352,708 B1 | 3/2002 | Duran et al. |
| 6,371,970 B1 | 4/2002 | Khosravi et al. |
| 6,371,983 B1 | 4/2002 | Lane |

(56) References Cited

U.S. PATENT DOCUMENTS

| | | |
|---|---|---|
| 6,380,457 B1 | 4/2002 | Yurek et al. |
| 6,398,807 B1 | 6/2002 | Chouinard et al. |
| 6,409,750 B1 | 6/2002 | Hyodoh et al. |
| 6,425,916 B1 | 7/2002 | Garrison et al. |
| 6,440,164 B1 | 8/2002 | DiMatteo et al. |
| 6,454,799 B1 | 9/2002 | Schreck |
| 6,458,153 B1 | 10/2002 | Bailey et al. |
| 6,461,382 B1 | 10/2002 | Cao |
| 6,468,303 B1 | 10/2002 | Amplatz et al. |
| 6,475,239 B1 | 11/2002 | Campbell et al. |
| 6,482,228 B1 | 11/2002 | Norred |
| 6,488,704 B1 | 12/2002 | Connelly et al. |
| 6,494,909 B2 | 12/2002 | Greenhalgh |
| 6,503,272 B2 | 1/2003 | Duerig et al. |
| 6,508,833 B2 | 1/2003 | Pavcnik et al. |
| 6,527,800 B1 | 3/2003 | McGuckin, Jr. et al. |
| 6,530,949 B2 | 3/2003 | Konya et al. |
| 6,530,952 B2 | 3/2003 | Vesely |
| 6,562,031 B2 | 5/2003 | Chandrasekaran et al. |
| 6,562,058 B2 | 5/2003 | Seguin et al. |
| 6,569,196 B1 | 5/2003 | Vesely |
| 6,585,758 B1 | 7/2003 | Chouinard et al. |
| 6,592,546 B1 | 7/2003 | Barbut et al. |
| 6,605,112 B1 | 8/2003 | Moll et al. |
| 6,613,077 B2 | 9/2003 | Gilligan et al. |
| 6,622,604 B1 | 9/2003 | Chouinard et al. |
| 6,632,243 B1 | 10/2003 | Zadno-Azizi et al. |
| 6,635,068 B1 | 10/2003 | Dubrul et al. |
| 6,652,571 B1 | 11/2003 | White et al. |
| 6,652,578 B2 | 11/2003 | Bailey et al. |
| 6,656,213 B2 | 12/2003 | Solem |
| 6,663,663 B2 | 12/2003 | Kim et al. |
| 6,669,724 B2 | 12/2003 | Park et al. |
| 6,673,089 B1 | 1/2004 | Yassour et al. |
| 6,673,109 B2 | 1/2004 | Cox |
| 6,676,698 B2 | 1/2004 | McGuckin, Jr. et al. |
| 6,682,558 B2 | 1/2004 | Tu et al. |
| 6,682,559 B2 | 1/2004 | Myers et al. |
| 6,685,739 B2 | 2/2004 | DiMatteo et al. |
| 6,689,144 B2 | 2/2004 | Gerberding |
| 6,689,164 B1 | 2/2004 | Seguin |
| 6,692,512 B2 | 2/2004 | Jang |
| 6,692,513 B2 | 2/2004 | Streeter et al. |
| 6,695,878 B2 | 2/2004 | McGuckin, Jr. et al. |
| 6,702,851 B1 | 3/2004 | Chinn et al. |
| 6,719,789 B2 | 4/2004 | Cox |
| 6,730,118 B2 | 5/2004 | Spenser et al. |
| 6,730,377 B2 | 5/2004 | Wang |
| 6,733,525 B2 | 5/2004 | Yang et al. |
| 6,736,846 B2 | 5/2004 | Cox |
| 6,752,828 B2 | 6/2004 | Thornton |
| 6,758,855 B2 | 7/2004 | Fulton, III et al. |
| 6,769,434 B2 | 8/2004 | Liddicoat et al. |
| 6,786,925 B1 | 9/2004 | Schoon |
| 6,790,229 B1 | 9/2004 | Berreklouw |
| 6,792,979 B2 | 9/2004 | Konya et al. |
| 6,797,002 B2 | 9/2004 | Spence |
| 6,821,297 B2 | 11/2004 | Snyders |
| 6,830,575 B2 | 12/2004 | Stenzel et al. |
| 6,830,584 B1 | 12/2004 | Seguin |
| 6,830,585 B1 | 12/2004 | Artof |
| 6,846,325 B2 | 1/2005 | Liddicoat |
| 6,866,650 B2 | 3/2005 | Stevens |
| 6,872,223 B2 | 3/2005 | Roberts |
| 6,875,231 B2 | 4/2005 | Anduiza et al. |
| 6,883,522 B2 | 4/2005 | Spence et al. |
| 6,887,266 B2 | 5/2005 | Williams et al. |
| 6,890,330 B2 | 5/2005 | Streeter et al. |
| 6,893,460 B2 | 5/2005 | Spenser et al. |
| 6,896,690 B1 | 5/2005 | Lambrecht et al. |
| 6,908,481 B2 | 6/2005 | Cribier |
| 6,913,600 B2 | 7/2005 | Valley et al. |
| 6,929,653 B2 | 8/2005 | Streeter |
| 6,936,066 B2 | 8/2005 | Palmaz et al. |
| 6,939,365 B1 | 9/2005 | Fogarty et al. |
| 6,951,571 B1 | 10/2005 | Srivastava |
| 6,986,742 B2 | 1/2006 | Hart et al. |
| 6,989,027 B2 | 1/2006 | Allen et al. |
| 6,989,028 B2 | 1/2006 | Lashinski et al. |
| 6,991,649 B2 | 1/2006 | Sievers |
| 7,018,401 B1 | 3/2006 | Hyodoh et al. |
| 7,041,128 B2 | 5/2006 | McGuckin, Jr. et al. |
| 7,044,966 B2 | 5/2006 | Svanidze et al. |
| 7,048,014 B2 | 5/2006 | Hyodoh et al. |
| 7,097,659 B2 | 8/2006 | Woolfson et al. |
| 7,101,396 B2 | 9/2006 | Artof et al. |
| 7,105,016 B2 | 9/2006 | Shui et al. |
| 7,115,141 B2 | 10/2006 | Menz et al. |
| 7,147,663 B1 | 12/2006 | Berg et al. |
| 7,153,324 B2 | 12/2006 | Case et al. |
| 7,160,319 B2 | 1/2007 | Chouinard et al. |
| 7,175,656 B2 | 2/2007 | Khairkhahan |
| 7,186,265 B2 | 3/2007 | Sharkawy et al. |
| 7,195,641 B2 | 3/2007 | Palmaz et al. |
| 7,198,646 B2 | 4/2007 | Figulla et al. |
| 7,201,761 B2 | 4/2007 | Woolfson et al. |
| 7,201,772 B2 | 4/2007 | Schwammenthal et al. |
| 7,252,682 B2 | 8/2007 | Seguin |
| 7,261,732 B2 | 8/2007 | Justino |
| 7,300,457 B2 | 11/2007 | Palmaz |
| 7,300,463 B2 | 11/2007 | Liddicoat |
| 7,316,706 B2 | 1/2008 | Bloom et al. |
| 7,329,278 B2 | 2/2008 | Seguin |
| 7,335,218 B2 | 2/2008 | Wilson et al. |
| 7,338,520 B2 | 3/2008 | Bailey et al. |
| 7,374,571 B2 | 5/2008 | Pease et al. |
| 7,381,218 B2 | 6/2008 | Schreck |
| 7,384,411 B1 | 6/2008 | Condado |
| 7,429,269 B2 | 9/2008 | Schwammenthal et al. |
| 7,442,204 B2 | 10/2008 | Schwammenthal et al. |
| 7,462,191 B2 | 12/2008 | Spenser et al. |
| 7,470,284 B2 | 12/2008 | Lambrecht et al. |
| 7,481,838 B2 | 1/2009 | Carpentier et al. |
| 7,544,206 B2 | 6/2009 | Cohn et al. |
| 7,556,646 B2 | 7/2009 | Yang et al. |
| 2001/0001314 A1 | 5/2001 | Davison et al. |
| 2001/0002445 A1 | 5/2001 | Vesely |
| 2001/0007956 A1 | 7/2001 | Letac et al. |
| 2001/0010017 A1 | 7/2001 | Letac et al. |
| 2001/0011189 A1 | 8/2001 | Drasler et al. |
| 2001/0021872 A1 | 9/2001 | Bailey et al. |
| 2001/0025196 A1 | 9/2001 | Chinn et al. |
| 2001/0032013 A1 | 10/2001 | Marton |
| 2001/0039450 A1 | 11/2001 | Pavcnik et al. |
| 2001/0041928 A1 | 11/2001 | Pavcnik et al. |
| 2001/0044647 A1 | 11/2001 | Pinchuk et al. |
| 2002/0010508 A1 | 1/2002 | Chobotov |
| 2002/0029014 A1 | 3/2002 | Jayaraman |
| 2002/0032480 A1 | 3/2002 | Spence et al. |
| 2002/0032481 A1 | 3/2002 | Gabbay |
| 2002/0035396 A1 | 3/2002 | Heath |
| 2002/0042650 A1 | 4/2002 | Vardi et al. |
| 2002/0052651 A1 | 5/2002 | Myers et al. |
| 2002/0058995 A1 | 5/2002 | Stevens |
| 2002/0072789 A1 | 6/2002 | Hackett et al. |
| 2002/0099439 A1 | 7/2002 | Schwartz et al. |
| 2002/0103533 A1 | 8/2002 | Langberg et al. |
| 2002/0107565 A1 | 8/2002 | Greenhalgh |
| 2002/0111674 A1 | 8/2002 | Chouinard et al. |
| 2002/0123802 A1 | 9/2002 | Snyders |
| 2002/0133183 A1 | 9/2002 | Lentz et al. |
| 2002/0138138 A1 | 9/2002 | Yang |
| 2002/0151970 A1 | 10/2002 | Garrison et al. |
| 2002/0161392 A1 | 10/2002 | Dubrul |
| 2002/0161394 A1 | 10/2002 | Macoviak et al. |
| 2002/0193871 A1 | 12/2002 | Beyersdorf et al. |
| 2003/0014104 A1 | 1/2003 | Cribier |
| 2003/0023300 A1 | 1/2003 | Bailey et al. |
| 2003/0023303 A1 | 1/2003 | Palmaz et al. |
| 2003/0028247 A1 | 2/2003 | Cali |
| 2003/0036791 A1 | 2/2003 | Philipp et al. |
| 2003/0040771 A1 | 2/2003 | Hyodoh et al. |
| 2003/0040772 A1 | 2/2003 | Hyodoh et al. |
| 2003/0040792 A1 | 2/2003 | Gabbay |

(56) References Cited

U.S. PATENT DOCUMENTS

| | | |
|---|---|---|
| 2003/0050694 A1 | 3/2003 | Yang et al. |
| 2003/0055495 A1 | 3/2003 | Pease et al. |
| 2003/0065386 A1 | 4/2003 | Weadock |
| 2003/0069492 A1 | 4/2003 | Abrams et al. |
| 2003/0109924 A1 | 6/2003 | Cribier |
| 2003/0125795 A1 | 7/2003 | Pavcnik et al. |
| 2003/0130726 A1 | 7/2003 | Thorpe et al. |
| 2003/0130729 A1 | 7/2003 | Paniagua et al. |
| 2003/0139804 A1 | 7/2003 | Hankh et al. |
| 2003/0149475 A1 | 8/2003 | Hyodoh et al. |
| 2003/0149476 A1 | 8/2003 | Damm et al. |
| 2003/0149478 A1 | 8/2003 | Figulla et al. |
| 2003/0153974 A1 | 8/2003 | Spenser et al. |
| 2003/0181850 A1 | 9/2003 | Diamond et al. |
| 2003/0191519 A1 | 10/2003 | Lombardi et al. |
| 2003/0199913 A1 | 10/2003 | Dubrul et al. |
| 2003/0199963 A1 | 10/2003 | Tower et al. |
| 2003/0199971 A1 | 10/2003 | Tower et al. |
| 2003/0199972 A1 | 10/2003 | Zadno-Azizi et al. |
| 2003/0212410 A1 | 11/2003 | Stenzel et al. |
| 2003/0212452 A1 | 11/2003 | Zadno-Azizi et al. |
| 2003/0212454 A1 | 11/2003 | Scott et al. |
| 2003/0225445 A1 | 12/2003 | Derus et al. |
| 2004/0030381 A1 | 2/2004 | Shu |
| 2004/0034411 A1 | 2/2004 | Quijano et al. |
| 2004/0039436 A1 | 2/2004 | Spenser et al. |
| 2004/0049224 A1 | 3/2004 | Buehlmann et al. |
| 2004/0049262 A1 | 3/2004 | Obermiller et al. |
| 2004/0049266 A1 | 3/2004 | Anduiza et al. |
| 2004/0082904 A1 | 4/2004 | Houde et al. |
| 2004/0088045 A1 | 5/2004 | Cox |
| 2004/0093005 A1 | 5/2004 | Durcan |
| 2004/0093060 A1 | 5/2004 | Seguin et al. |
| 2004/0097788 A1 | 5/2004 | Mourles et al. |
| 2004/0098112 A1 | 5/2004 | DiMatteo et al. |
| 2004/0106976 A1 | 6/2004 | Bailey et al. |
| 2004/0106990 A1 | 6/2004 | Spence et al. |
| 2004/0111096 A1 | 6/2004 | Tu et al. |
| 2004/0116951 A1 | 6/2004 | Rosengart |
| 2004/0117004 A1 | 6/2004 | Osborne et al. |
| 2004/0122468 A1 | 6/2004 | Yodfat et al. |
| 2004/0122516 A1 | 6/2004 | Fogarty |
| 2004/0127979 A1 | 7/2004 | Wilson |
| 2004/0138742 A1 | 7/2004 | Myers et al. |
| 2004/0138743 A1 | 7/2004 | Myers et al. |
| 2004/0153146 A1 | 8/2004 | Lashinski et al. |
| 2004/0167573 A1 | 8/2004 | Williamson |
| 2004/0167620 A1 | 8/2004 | Ortiz |
| 2004/0186563 A1 | 9/2004 | Iobbi |
| 2004/0193261 A1 | 9/2004 | Berreklouw |
| 2004/0210240 A1 | 10/2004 | Saint |
| 2004/0210304 A1 | 10/2004 | Seguin et al. |
| 2004/0210305 A1 | 10/2004 | Shu et al. |
| 2004/0210307 A1 | 10/2004 | Khairkhahan |
| 2004/0215333 A1 | 10/2004 | Duran |
| 2004/0215339 A1 | 10/2004 | Drasler et al. |
| 2004/0225353 A1 | 11/2004 | McGuckin, Jr. |
| 2004/0225354 A1 | 11/2004 | Allen |
| 2004/0254636 A1 | 12/2004 | Flagle et al. |
| 2004/0260394 A1 | 12/2004 | Douk et al. |
| 2004/0267357 A1 | 12/2004 | Allen et al. |
| 2005/0010246 A1 | 1/2005 | Streeter |
| 2005/0010285 A1 | 1/2005 | Lambrecht et al. |
| 2005/0010287 A1 | 1/2005 | Macoviak |
| 2005/0015112 A1 | 1/2005 | Cohn et al. |
| 2005/0027348 A1 | 2/2005 | Case et al. |
| 2005/0033398 A1 | 2/2005 | Seguin |
| 2005/0043790 A1 | 2/2005 | Seguin |
| 2005/0049692 A1 | 3/2005 | Numamoto |
| 2005/0049696 A1 | 3/2005 | Siess |
| 2005/0055088 A1 | 3/2005 | Liddicoat et al. |
| 2005/0060029 A1 | 3/2005 | Le |
| 2005/0060030 A1 | 3/2005 | Lashinski et al. |
| 2005/0075584 A1 | 4/2005 | Cali |
| 2005/0075712 A1 | 4/2005 | Biancucci |
| 2005/0075717 A1 | 4/2005 | Nguyen |
| 2005/0075719 A1 | 4/2005 | Bergheim |
| 2005/0075724 A1 | 4/2005 | Svanidze |
| 2005/0075727 A1 | 4/2005 | Wheatley |
| 2005/0075730 A1 | 4/2005 | Myers |
| 2005/0075731 A1 | 4/2005 | Artof |
| 2005/0085842 A1 | 4/2005 | Eversull et al. |
| 2005/0085843 A1 | 4/2005 | Opolski et al. |
| 2005/0085890 A1 | 4/2005 | Rasmussen et al. |
| 2005/0085900 A1 | 4/2005 | Case et al. |
| 2005/0096568 A1 | 5/2005 | Kato |
| 2005/0096692 A1 | 5/2005 | Linder et al. |
| 2005/0096724 A1 | 5/2005 | Stenzel et al. |
| 2005/0096734 A1 | 5/2005 | Majercak et al. |
| 2005/0096735 A1 | 5/2005 | Hojeibane et al. |
| 2005/0096736 A1 | 5/2005 | Osse et al. |
| 2005/0096738 A1 | 5/2005 | Cali et al. |
| 2005/0107871 A1 | 5/2005 | Realyvasquez et al. |
| 2005/0113910 A1 | 5/2005 | Paniagua |
| 2005/0119688 A1 | 6/2005 | Bergheim |
| 2005/0131438 A1 | 6/2005 | Cohn |
| 2005/0137686 A1 | 6/2005 | Salahieh |
| 2005/0137688 A1 | 6/2005 | Salahieh et al. |
| 2005/0137692 A1 | 6/2005 | Haug |
| 2005/0137695 A1 | 6/2005 | Salahieh |
| 2005/0137701 A1 | 6/2005 | Salahieh |
| 2005/0143809 A1 | 6/2005 | Salahieh |
| 2005/0148997 A1 | 7/2005 | Valley et al. |
| 2005/0149181 A1 | 7/2005 | Eberhardt |
| 2005/0165477 A1 | 7/2005 | Anduiza et al. |
| 2005/0187616 A1 | 8/2005 | Realyvasquez |
| 2005/0203549 A1 | 9/2005 | Realyvasquez |
| 2005/0203605 A1 | 9/2005 | Dolan |
| 2005/0203615 A1 | 9/2005 | Forster et al. |
| 2005/0203618 A1 | 9/2005 | Sharkawy |
| 2005/0222674 A1 | 10/2005 | Paine |
| 2005/0228495 A1 | 10/2005 | Macoviak |
| 2005/0234546 A1 | 10/2005 | Nugent |
| 2005/0240200 A1 | 10/2005 | Bergheim |
| 2005/0240263 A1 | 10/2005 | Fogarty et al. |
| 2005/0261759 A1 | 11/2005 | Lambrecht et al. |
| 2005/0283962 A1 | 12/2005 | Boudjemline |
| 2006/0004439 A1 | 1/2006 | Spenser et al. |
| 2006/0004469 A1 | 1/2006 | Sokel |
| 2006/0009841 A1 | 1/2006 | McGuckin et al. |
| 2006/0052867 A1 | 3/2006 | Revuelta et al. |
| 2006/0058775 A1 | 3/2006 | Stevens et al. |
| 2006/0089711 A1 | 4/2006 | Dolan |
| 2006/0100685 A1 | 5/2006 | Seguin et al. |
| 2006/0116757 A1 | 6/2006 | Lashinski et al. |
| 2006/0135964 A1 | 6/2006 | Vesely |
| 2006/0142848 A1 | 6/2006 | Gabbay |
| 2006/0167474 A1 | 7/2006 | Bloom et al. |
| 2006/0178740 A1 | 8/2006 | Stacchino et al. |
| 2006/0195134 A1 | 8/2006 | Crittenden |
| 2006/0195184 A1 | 8/2006 | Lane et al. |
| 2006/0206192 A1 | 9/2006 | Tower et al. |
| 2006/0206202 A1 | 9/2006 | Bonhoefer et al. |
| 2006/0235509 A1 | 10/2006 | Lafontaine |
| 2006/0247763 A1 | 11/2006 | Slater |
| 2006/0259134 A1 | 11/2006 | Schwammenthal et al. |
| 2006/0259136 A1 | 11/2006 | Nguyen et al. |
| 2006/0259137 A1 | 11/2006 | Artof et al. |
| 2006/0265056 A1 | 11/2006 | Nguyen et al. |
| 2006/0271166 A1 | 11/2006 | Thill et al. |
| 2006/0271175 A1 | 11/2006 | Woolfson et al. |
| 2006/0276874 A1 | 12/2006 | Wilson et al. |
| 2006/0282161 A1 | 12/2006 | Huynh et al. |
| 2006/0293745 A1 | 12/2006 | Carpentier et al. |
| 2007/0005129 A1 | 1/2007 | Damm et al. |
| 2007/0005131 A1 | 1/2007 | Taylor |
| 2007/0010878 A1 | 1/2007 | Raffiee et al. |
| 2007/0016286 A1 | 1/2007 | Herrmann et al. |
| 2007/0027518 A1 | 2/2007 | Case et al. |
| 2007/0027533 A1 | 2/2007 | Douk |
| 2007/0043435 A1 | 2/2007 | Seguin et al. |
| 2007/0051377 A1 | 3/2007 | Douk et al. |
| 2007/0073392 A1 | 3/2007 | Heyninck-Janitz |
| 2007/0078509 A1 | 4/2007 | Lotfy et al. |

(56) References Cited

U.S. PATENT DOCUMENTS

| | | |
|---|---|---|
| 2007/0078510 A1 | 4/2007 | Ryan |
| 2007/0088431 A1 | 4/2007 | Bourang et al. |
| 2007/0093869 A1 | 4/2007 | Bloom et al. |
| 2007/0100439 A1 | 5/2007 | Cangialosi |
| 2007/0100440 A1 | 5/2007 | Figulla |
| 2007/0100449 A1 | 5/2007 | O'Neil et al. |
| 2007/0112415 A1 | 5/2007 | Bartlett |
| 2007/0142896 A1 | 6/2007 | Anderson et al. |
| 2007/0162102 A1 | 7/2007 | Ryan et al. |
| 2007/0162113 A1 | 7/2007 | Sharkawy et al. |
| 2007/0185513 A1 | 8/2007 | Woolfson et al. |
| 2007/0203391 A1 | 8/2007 | Bloom et al. |
| 2007/0225681 A1 | 9/2007 | House |
| 2007/0232898 A1 | 10/2007 | Huynh et al. |
| 2007/0233228 A1 | 10/2007 | Eberhardt et al. |
| 2007/0233237 A1 | 10/2007 | Krivoruchko |
| 2007/0233238 A1 | 10/2007 | Huynh et al. |
| 2007/0238979 A1 | 10/2007 | Huynh et al. |
| 2007/0239254 A1 | 10/2007 | Chia et al. |
| 2007/0239265 A1 | 10/2007 | Birdsall |
| 2007/0239266 A1 | 10/2007 | Birdsall |
| 2007/0239269 A1 | 10/2007 | Dolan et al. |
| 2007/0239273 A1 | 10/2007 | Allen |
| 2007/0244544 A1 | 10/2007 | Birdsall et al. |
| 2007/0244545 A1 | 10/2007 | Birdsall et al. |
| 2007/0244546 A1 | 10/2007 | Francis |
| 2007/0244553 A1 | 10/2007 | Rafiee et al. |
| 2007/0244554 A1 | 10/2007 | Rafiee et al. |
| 2007/0244555 A1 | 10/2007 | Rafiee et al. |
| 2007/0244556 A1 | 10/2007 | Rafiee et al. |
| 2007/0244557 A1 | 10/2007 | Rafiee et al. |
| 2007/0250160 A1 | 10/2007 | Rafiee |
| 2007/0255394 A1 | 11/2007 | Ryan |
| 2007/0255396 A1 | 11/2007 | Douk et al. |
| 2007/0288000 A1 | 12/2007 | Bonan |
| 2008/0004696 A1 | 1/2008 | Vesely |
| 2008/0009940 A1 | 1/2008 | Cribier |
| 2008/0015671 A1 | 1/2008 | Bonhoeffer |
| 2008/0021552 A1 | 1/2008 | Gabbay |
| 2008/0048656 A1 | 2/2008 | Tan |
| 2008/0065001 A1 | 3/2008 | Marchand et al. |
| 2008/0065206 A1 | 3/2008 | Liddicoat |
| 2008/0071361 A1 | 3/2008 | Tuval et al. |
| 2008/0071362 A1 | 3/2008 | Tuval et al. |
| 2008/0071363 A1 | 3/2008 | Tuval et al. |
| 2008/0071366 A1 | 3/2008 | Tuval et al. |
| 2008/0071368 A1 | 3/2008 | Tuval et al. |
| 2008/0077234 A1 | 3/2008 | Styrc |
| 2008/0082165 A1 | 4/2008 | Wilson et al. |
| 2008/0082166 A1 | 4/2008 | Styrc et al. |
| 2008/0133003 A1 | 6/2008 | Seguin et al. |
| 2008/0140189 A1 | 6/2008 | Nguyen et al. |
| 2008/0147105 A1 | 6/2008 | Wilson et al. |
| 2008/0147180 A1 | 6/2008 | Ghione et al. |
| 2008/0147181 A1 | 6/2008 | Ghione et al. |
| 2008/0147182 A1 | 6/2008 | Righini et al. |
| 2008/0154355 A1 | 6/2008 | Benichow et al. |
| 2008/0154356 A1 | 6/2008 | Obermiller et al. |
| 2008/0161910 A1 | 7/2008 | Revuelta et al. |
| 2008/0161911 A1 | 7/2008 | Revuelta et al. |
| 2008/0183273 A1 | 7/2008 | Mesana et al. |
| 2008/0188928 A1 | 8/2008 | Salahieh et al. |
| 2008/0215143 A1 | 9/2008 | Seguin et al. |
| 2008/0215144 A1 | 9/2008 | Ryan et al. |
| 2008/0228254 A1 | 9/2008 | Ryan |
| 2008/0228263 A1 | 9/2008 | Ryan |
| 2008/0234797 A1 | 9/2008 | Styrc |
| 2008/0243246 A1 | 10/2008 | Ryan et al. |
| 2008/0255651 A1 | 10/2008 | Dwork |
| 2008/0255660 A1 | 10/2008 | Guyenot et al. |
| 2008/0255661 A1 | 10/2008 | Straubinger et al. |
| 2008/0262593 A1 | 10/2008 | Ryan et al. |
| 2009/0005863 A1 | 1/2009 | Goetz et al. |
| 2009/0012600 A1 | 1/2009 | Styrc et al. |
| 2009/0048656 A1 | 2/2009 | Wen |
| 2009/0054976 A1 | 2/2009 | Tuval et al. |
| 2009/0069886 A1 | 3/2009 | Suri et al. |
| 2009/0069887 A1 | 3/2009 | Righini et al. |
| 2009/0069889 A1 | 3/2009 | Suri et al. |
| 2009/0138079 A1 | 5/2009 | Tuval et al. |
| 2009/0164004 A1 | 6/2009 | Cohn |
| 2009/0171447 A1 | 7/2009 | VonSegesser et al. |
| 2009/0192585 A1 | 7/2009 | Bloom et al. |
| 2009/0192586 A1 | 7/2009 | Tabor et al. |
| 2009/0192591 A1 | 7/2009 | Ryan et al. |
| 2009/0198316 A1 | 8/2009 | Laske et al. |
| 2009/0216310 A1 | 8/2009 | Straubinger et al. |
| 2009/0216312 A1 | 8/2009 | Straubinger et al. |
| 2009/0216313 A1 | 8/2009 | Straubinger et al. |
| 2009/0240264 A1 | 9/2009 | Tuval et al. |
| 2009/0240320 A1 | 9/2009 | Tuval |
| 2010/0049306 A1 | 2/2010 | House et al. |
| 2010/0094411 A1 | 4/2010 | Tuval et al. |
| 2010/0100167 A1 | 4/2010 | Bortlein et al. |
| 2010/0131054 A1 | 5/2010 | Tuval et al. |
| 2010/0137979 A1 | 6/2010 | Tuval et al. |
| 2010/0179649 A1 | 7/2010 | Richter et al. |

FOREIGN PATENT DOCUMENTS

| | | |
|---|---|---|
| DE | 195 46 692 C2 | 6/1997 |
| DE | 198 57 887 A1 | 7/2000 |
| DE | 199 07 646 | 8/2000 |
| DE | 100 48 814 | 9/2000 |
| DE | 100 49 812 | 4/2002 |
| DE | 100 49 813 | 4/2002 |
| DE | 100 49 815 | 4/2002 |
| EP | 0103546 | 3/1984 |
| EP | 0597967 | 12/1994 |
| EP | 1057459 A1 | 6/2000 |
| EP | 1057460 A1 | 6/2000 |
| EP | 1088529 | 4/2001 |
| EP | 1255510 | 11/2002 |
| EP | 0937439 B1 | 9/2003 |
| EP | 1340473 | 9/2003 |
| EP | 1356792 | 10/2003 |
| EP | 0819013 | 6/2004 |
| EP | 1872743 | 1/2008 |
| FR | 2788217 | 12/1999 |
| GB | 2056023 | 3/1981 |
| GB | 2433700 | 12/2007 |
| WO | 91/17720 | 11/1991 |
| WO | 93/01768 | 2/1993 |
| WO | 95/29640 | 11/1995 |
| WO | 98/14137 | 4/1998 |
| WO | 98/29057 | 7/1998 |
| WO | 99/33414 | 7/1999 |
| WO | 00/41652 | 7/2000 |
| WO | 00/44313 | 8/2000 |
| WO | 00/47136 | 8/2000 |
| WO | 00/47139 | 8/2000 |
| WO | 01/35870 | 5/2001 |
| WO | 01/49213 | 7/2001 |
| WO | 01/54625 | 8/2001 |
| WO | 01/62189 | 8/2001 |
| WO | 01/64137 | 9/2001 |
| WO | 01/76510 | 10/2001 |
| WO | 02/22054 | 3/2002 |
| WO | 02/36048 | 5/2002 |
| WO | 02/41789 | 5/2002 |
| WO | 02/43620 | 6/2002 |
| WO | 02/47575 | 6/2002 |
| WO | 02/49540 | 6/2002 |
| WO | 03/003943 | 1/2003 |
| WO | 03/003949 | 1/2003 |
| WO | 03/011195 | 2/2003 |
| WO | 03/030776 | 4/2003 |
| WO | 2004/019811 | 3/2004 |
| WO | 2004/019825 | 3/2004 |
| WO | 2004/023980 | 3/2004 |
| WO | 2004/041126 | 5/2004 |
| WO | 2004/058106 | 7/2004 |
| WO | 2004/089250 | 10/2004 |
| WO | 2005/004753 | 1/2005 |

(56) References Cited

FOREIGN PATENT DOCUMENTS

| WO | 2005/027790 | 3/2005 |
|---|---|---|
| WO | 2005/046528 | 5/2005 |
| WO | 2006/026371 | 3/2006 |
| WO | 2008/047354 | 4/2008 |
| WO | 2008/100599 | 8/2008 |
| WO | 2008/150529 | 12/2008 |
| WO | 2009/002548 | 12/2008 |
| WO | 2009/029199 | 3/2009 |
| WO | 2009/042196 | 4/2009 |
| WO | 2009/045338 | 4/2009 |
| WO | 2009/061389 | 5/2009 |
| WO | 2009/091509 | 7/2009 |
| WO | 2009/111241 | 9/2009 |

OTHER PUBLICATIONS

Andersen, H.R. et al, "Transluminal implantation of artificial heart valves. Description of a new expandable aortic valve and initial results with implantation by catheter technique in closed chest pigs." Euro. Heart J. (1992) 13:704-708.
Babaliaros, et al., "State of the Art Percutaneous Intervention for the Treatment of Valvular Heart Disease: A Review of the Current Technologies and Ongoing Research in the Field of Percutaneous Heart Valve Replacement and Repair," Cardiology 2007; 107:87-96.
Bailey, "Percutaneous Expandable Prosthetic Valves," In: Topol EJ, ed. Textbook of Interventional Cardiology. vol. II. Second edition. WB Saunders, Philadelphia, 1994:1268-1276.
Block, et al., "Percutaneous Approaches to Valvular Heart Disease," Current Cardiology Reports, vol. 7 (2005) pp. 108-113.
Bonhoeffer, et al, "Percutaneous Insertion of the Pulmonary Valve," Journal of the American College of Cardiology (United States), May 15, 2002, pp. 1664-1669.
Bonhoeffer, et al, "Percutaneous Mitral Valve Dilatation with the Multi-Track System," Catheterization and Cardiovascular Interventions—Official Journal of the Society for Cardiac Angiography & Interventions (United States), Oct. 1999, pp. 178-183.
Bonhoeffer, et al, "Percutaneous Replacement of Pulmonary Valve in a Right-Ventricle to Pulmonary-Artery Prosthetic Conduit with Valve Dysfunction," Lancet (England), Oct. 21, 2000, pp. 1403-1405.
Bonhoeffer, et al, "Transcatheter Implantation of a Bovine Valve in Pulmonary Position: A Lamb Study," Circulation (United States), Aug. 15, 2000, pp. 813-816.
Boudjemline, et al, "Images in Cardiovascular Medicine. Percutaneous Aortic Valve Replacement in Animals," Circulation (United States), Mar. 16, 2004, 109, p. e161.
Boudjemline, et al, "Is Percutaneous Implantation of a Bovine Venous Valve in the Inferior Vena Cava a Reliable Technique to Treat Chronic Venous Insufficiency Syndrome?" Medical Science Monitor—International Medical Journal of Experimental and Clinical Research (Poland), Mar. 2004, pp. BR61-BR66.
Boudjemline, et al, "Off-pump Replacement of the Pulmonary Valve in Large Right Ventricular Outflow Tracts: A Hybrid Approach," Journal of Thoracic and Cardiovascular Surgery (United States), Apr. 2005, pp. 831-837.
Boudjemline, et al, "Percutaneous Aortic Valve Replacement: Will We Get There?" Heart (British Cardiac Society) (England), Dec. 2001, pp. 705-706.
Boudjemline, et al, "Percutaneous Closure of a Paravalvular Mitral Regurgitation with Amplatzer and Coil Prostheses," Archives des Maladies du Coeur Et Des Vaisseaux (France), May 2002, pp. 483-486.
Boudjemline, et al, "Percutaneous Implantation of a Biological Valve in the Aorta to Treat Aortic Valve Insufficiency—A Sheep Study," Medical Science Monitor—International Medical Journal of Experimental and Clinical Research (Poland), Apr. 2002, pp. BR113-BR116.
Boudjemline, et al, "Percutaneous Implantation of a Biological Valve in Aortic Position: Preliminary Results in a Sheep Study," European Heart Journal 22, Sep. 2001, p. 630.
Boudjemline, et al, "Percutaneous Implantation of a Valve in the Descending Aorta in Lambs," European Heart Journal (England), Jul. 2002, pp. 1045-1049.
Boudjemline, et al, "Percutaneous Pulmonary Valve Replacement in a Large Right Ventricular Outflow Tract: An Experimental Study," Journal of the American College of Cardiology (United States), Mar. 17, 2004, pp. 1082-1087.
Boudjemline, et al, "Percutaneous Valve Insertion: A New Approach," Journal of Thoracic and Cardiovascular Surgery (United States), Mar. 2003, pp. 741-742.
Boudjemline, et al, "Stent Implantation Combined with a Valve Replacement to Treat Degenerated Right Ventricle to Pulmonary Artery Prosthetic Conduits," European Heart Journal 22, Sep. 2001, p. 355.
Boudjemline, et al, "Steps Toward Percutaneous Aortic Valve Replacement," Circulation (United States), Feb. 12, 2002, pp. 775-778.
Boudjemline, et al, "The Percutaneous Implantable Heart Valve," Progress in Pediatric Cardiology (Ireland), 2001, pp. 89-93.
Boudjemline, et al, "Transcatheter Reconstruction of the Right Heart," Cardiology in the Young (England), Jun. 2003, pp. 308-311.
Coats, et al, "The Potential Impact of Percutaneous Pulmonary Valve Stent Implantation on Right Ventricular Outflow Tract Re-Intervention," European Journal of Cardio-Thoracic Surgery (England), Apr. 2005, pp. 536-543.
Cribier, A. et al, "Percutaneous Transcatheter Implantation of an Aortic Valve Prosthesis for Calcific Aortic Stenosis: First Human Case Description," Circulation (2002) 3006-3008.
Davidson et al., "Percutaneous therapies for valvular heart disease," Cardiovascular Pathology 15 (2006) 123-129.
Henzel, et al., "Complications of percutaneous aortic valve replacement: experience with the Criber-Edwards® percutaneous heart valve," EuroIntervention Supplements (2006), 1 (Supplement A) A3-A8.
Huber, et al., "Do Valved Stents Compromise Coronary Flow?" Eur. J. Cardiothorac. Surg. 2004;25:754-759.
Khambadkone, "Nonsurgical Pulmonary Valve Replacement: Why, When, and How?" Catheterization and Cardiovascular Interventions—Official Journal of the Society for Cardiac Angiography & Interventions (United States), Jul. 2004, pp. 401-408.
Khambadkone, et al, "Percutaneous Implantation of Pulmonary Valves," Expert Review of Cardiovascular Therapy (England), Nov. 2003, pp. 541-548.
Khambadkone, et al, "Percutaneous Pulmonary Valve Implantation: Early and Medium Term Results," Circulation 108 (17 Supplement), Oct. 28, 2003, p. IV-375.
Khambadkone, et al, "Percutaneous Pulmonary Valve Implantation: Impact of Morphology on Case Selection," Circulation 108 (17 Supplement), Oct. 28, 2003, p. IV-642-IV-643.
Lutter, et al, "Percutaneous Aortic Valve Replacement: An Experimental Study. I. Studies on Implantation," The Journal of Thoracic and Cardiovascular Surgery, Apr. 2002, pp. 768-776.
Lutter, et al, "Percutaneous Valve Replacement: Current State and Future Prospects," Annals of Thoracic Surgery (Netherlands), Dec. 2004, pp. 2199-2206.
Medtech Insight, "New Frontiers in Heart Valve Disease," vol. 7, No. 8 (2005).
Palacios, "Percutaneous Valve Replacement and Repair, Fiction or Reality?" Journal of American College of Cardiology, vol. 44, No. 8 (2004) pp. 1662-1663.
Pelton et al., "Medical Uses of Nitinol," Materials Science Forum vols. 327-328, pp. 63-70 (2000).
Ruiz, "Transcathether Aortic Valve Implantation and Mitral Valve Repair: State of the Art," Pediatric Cardiology, vol. 26, No. 3 (2005).
Saliba, et al, "Treatment of Obstructions of Prosthetic Conduits by Percutaneous Implantation of Stents," Archives des Maldies du Coeur et des Vaisseaux (France), 1999, pp. 591-596.
Webb, et al., "Percutaneous Aortic Valve Implantation Retrograde from the Femoral Artery," Circulation (2006), 113;842-850.
Stassano et al., "Mid-term results of the valve-on-valve technique for bioprosthetic failure," Eur. J. Cardiothorac. Surg. 2000; 18:453-457.

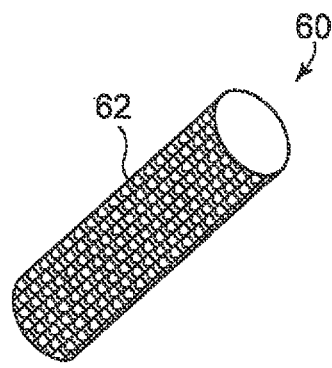
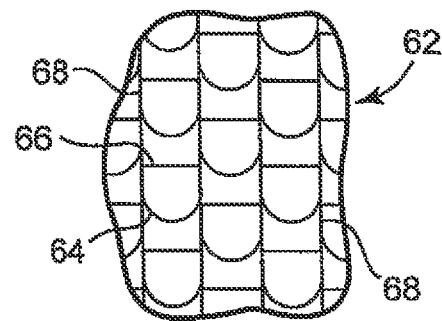
Fig. 8  Fig. 9
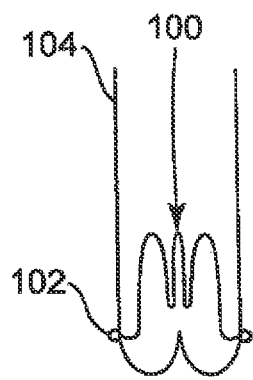
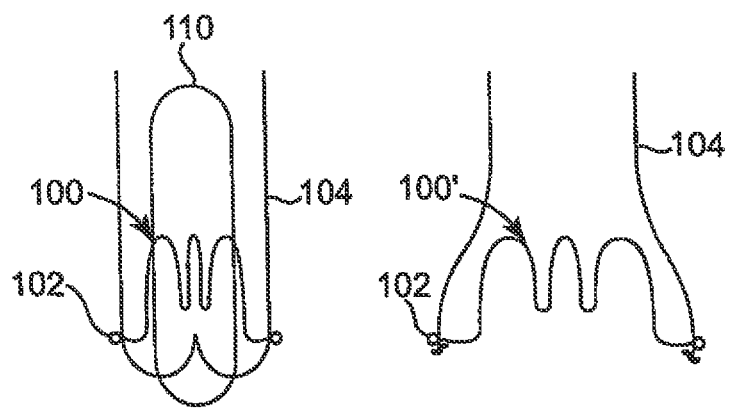
Fig. 10  Fig. 11  Fig. 12

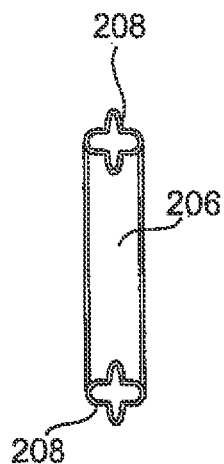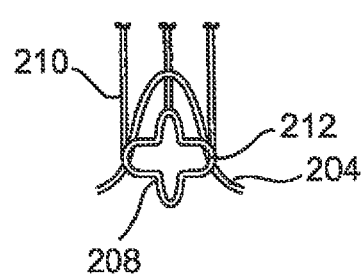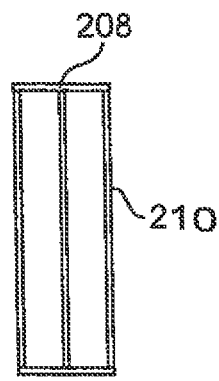
Fig. 18  Fig. 19  Fig. 20
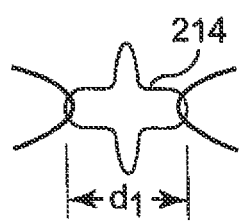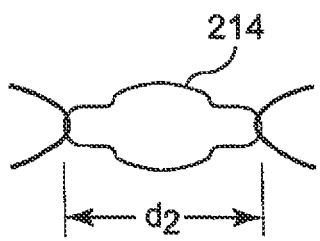
Fig. 21  Fig. 22
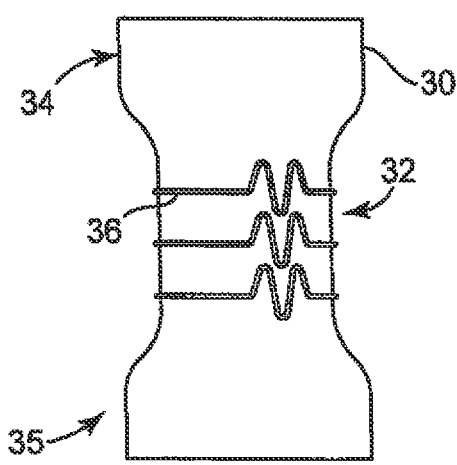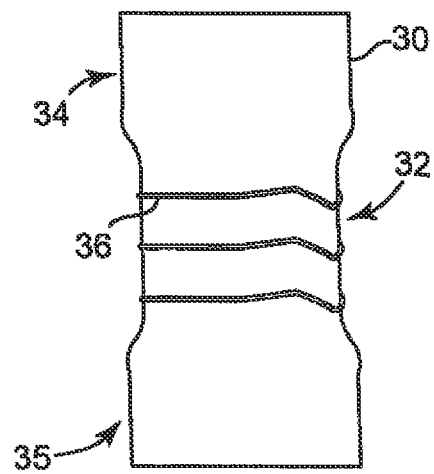
Fig. 23  Fig. 24

PROSTHETIC HEART VALVE SYSTEMS

CROSS-REFERENCE TO RELATED APPLICATIONS

The present application is a division of and claims the benefit of U.S. patent application Ser. No. 13/178,112 filed Jul. 7, 2011, which is a continuation of U.S. application Ser. No. 12/380,483, filed Feb. 27, 2009 and titled "Prosthetic Heart Valve Systems", which claims priority to U.S. Provisional Application No. 61/032,185, filed Feb. 28, 2008, and titled "Prosthetic Heart Valve Systems," the entire contents of which are incorporated herein by reference in their entireties.

TECHNICAL FIELD

The present invention relates to prosthetic heart valves. More particularly, it relates to transcatheter implants, methods, and delivery systems.

BACKGROUND

Heart valve replacement surgery involves the replacement of the native valves of the heart with a prosthetic valve. Prosthetic valves include mechanical valves involving only metals and polymers, and tissue valves that include non-synthetic, biocompatible materials such as pericardium, or bovine, equine or porcine tissue. Some patients have a relatively small aortic root due to their particular anatomy or excessive calcification. Some patients (e.g., young children) are likely to outgrow a prosthetic valve or outlive the useful life of a prosthetic valve.

U.S. Pat. No. 5,383,926 (Lock et al.) discloses a re-expandable endoprosthesis. The endoprosthesis is said to be re-expandable to accommodate vessel change.

U.S. Patent Application Publication Nos. 2003/0199971 A1 (Tower et al) and 2003/0199963 A1 (Tower et al.) describe a valved segment of bovine jugular vein mounted within an expandable stent, for use as a replacement heart valve. Replacement pulmonary valves may be implanted to replace native pulmonary valves or prosthetic pulmonary valves located in valved conduits as described, for example, in "Percutaneous Insertion of the Pulmonary Valve", Bonhoeffer, et al., Journal of the American College of Cardiology 2002; 39: 1664-1669.

Degenerated and stenotic valves in conduits or in valved stents potentially allow for a second valved stent implantation without the need for surgery, as described, for example, in "Transcatheter Replacement of a Bovine Valve in Pulmonary Position", Bonhoeffer, et al., Circulation 2000; 102: 813-816. It has been proposed that sequential percutaneous pulmonary valve implantation is feasible and theoretically could delay the need for invasive surgery indefinitely, thus overcoming concerns regarding conduit longevity and risks associated with reoperation, as described, for example, in "The potential impact of percutaneous pulmonary valve stent implantation on right ventricular outflow tract re-intervention", Coates, et al., European journal of Cardio-thoracic Surgery 27 (2005) 536-543.

U.S. Patent Application Publication No. 2003/0199971 A1 (Tower et al.) discloses a stented valve with an ability to be reconfigured after implantation. This is identified as a feature useful in cases where a valve has been implanted in a growing patient (e.g., a child). Rather than replacing a valve periodically during the growth period, the supporting stent may be reconfigured to accommodate growth using a percutaneously introduced balloon catheter for re-engaging the stent to reconfigure the stent so that it will conform to the changes in the implantation site produced by the growth of the patient. In an article by Bonhoeffer, et al. entitled "Percutaneous Insertion of the Pulmonary Valve" J Am Coll Cardiol, 2002; 39:1664-1669, the percutaneous delivery of a biological valve is described. The valve is sutured to an expandable stent within a previously implanted valved or non-valved conduit, or a previously implanted valve. Again, radial expansion of the secondary valve stent is used for placing an maintaining the replacement valve.

Stented valve systems involving two or more components are disclosed in U.S. Patent Application Nos. 2004/0030381 A1 (Shu et al.) and 2008/0004696 A1 (Vesely et al.); U.S. Pat. No. 6,530,052 (Khou et al.) and U.S. Pat. No. 7,011,681 (Vesely et al.) and PCT Publication Nos. WO 06/0127756 A2 (Rowe et al.), WO 07/0181820 (Nugent et al.) and WO 07/130537 (Lock et al.). Some of these valve systems describe the reuse of a portion of their system. Some of these valve systems require the removal of an element and its replacement by a different element. It is believed that transcatheter removal of a previously implanted stented valve component creates challenges such as damage to implant site, creation of sites for thrombus/emboli formation and release, paravalvular leakage, inability to access removable elements due to tissue ingrowth and/or complex navigation, and delivery difficulties.

SUMMARY

The present invention is directed to a heart valve that can be expanded following its implantation in a patient. In one aspect of the present invention, the expansion can accommodate the growth of a patient and the corresponding growth of the area where the valve is implanted. In another aspect, the present invention may maximize the orifice size of the surgical valve. The present invention includes expandable implantable conduits and expandable bioprosthetic stented valves. In one aspect of the invention, the valve may be adapted to accommodate growth of a patient to address limitation on bioprosthetic valve lifespans.

The heart valves of the invention may also facilitate a subsequent minimally invasive intervention for replacement of all or part of the valve system. In another aspect, the heart valves of the invention may ease the implantation process and could accommodate the use of a larger valve, which is especially useful for a patient with a small annulus (e.g., a small aortic annulus).

The heart valves of the invention have the capacity to overcome concerns regarding conduit longevity and risks associated with performing multiple surgeries in the same area of the patient. The heart valves of the present invention advantageously utilize the proven attributes of surgical valves (e.g., durability), while addressing some of the shortcomings of surgical valves. In particular, the heart valves of the invention provide the ability to expand a valve post implant, which provides a number of major advantages that have yet to be proven clinically in humans. First, surgical tissue valves are typically offered in a limited number of sizes/diameters. The post-implant transcatheter surgical valve expansion provided by the valves of the invention enables the orifice size for each surgical prosthetic valve patient to be maximized post-implant, thereby improving valve function. Second, the post-implant surgical valve transcatheter expansion provided by the valves of the invention enables the orifice for each surgical prosthetic valve pediatric patient to be adjusted post-implant, to thereby accommodate patient growth and eliminate unnecessary surgeries. Third, the post-implant transcatheter surgical valve expansion provided by the valves of the invention increases the orifice size of the surgical prosthetic valve patient to accommodate a larger transcatheter valve after failure of the surgical valve, thereby eliminating the need for surgical replacement. Fourth, the post-implant transcatheter surgical valve expansion provided by the valves of the invention enables clinicians to implant transcatheter valves inside small bioprosthetic valves with improved hemodynamic results. Fifth, the post-implant transcatheter surgical valve expansion provided by the valves of the invention may enable implantation of bioprosthetic valves into younger patients by facilitating transcatheter valve replacement once the bioprosthetic valve fails or presents severe risk of failure.

In another aspect of the invention, surgical methods are provided. In one embodiment, the method comprises implanting a surgical valve in an efficient manner. For example, some patients have a small aortic annulus. The present invention affords implantation of a valve in an undersized condition, after which the valve may be expanded to be larger in size or diameter (e.g., with a balloon), such as after the patient grows, minimizing the need for re-operation due to inadequate orifice size.

BRIEF DESCRIPTION OF THE DRAWINGS

The present invention will be further explained with reference to the appended Figures, wherein like structure is referred to by like numerals throughout the several views, and wherein:

FIG. 8 is a perspective view of an expandable component of another embodiment of the invention;

FIG. 9 is an enlarged front schematic view of a portion of the expandable component of FIG. 8;

FIG. 10 is a front schematic view of an embodiment of a heart valve of the invention that is implanted in a first, unexpanded condition;

FIG. 11 is a front schematic view of a balloon being used to expand the heart valve of FIG. 10 toward an expanded condition;

FIG. 12 is a front schematic view of the heart valve of FIG. 10 after it has been expanded;

FIG. 18 is a partial cross-sectional view of a seam expansion member of the invention;

FIG. 19 is a bottom perspective view of a portion of the expansion member of FIG. 18;

FIG. 20 is a front view of the expansion member of FIG. 18;

FIG. 21 is a side view of another embodiment of an expansion member of the invention;

FIG. 22 is another side view of the expansion member of FIG. 21;

FIG. 23 is a front view of another embodiment of an expandable conduit of the invention in a relatively unexpanded state; and FIG. 24 is a front view of the conduit of FIG. 23 in a relatively expanded state.

DETAILED DESCRIPTION

Figure 1:
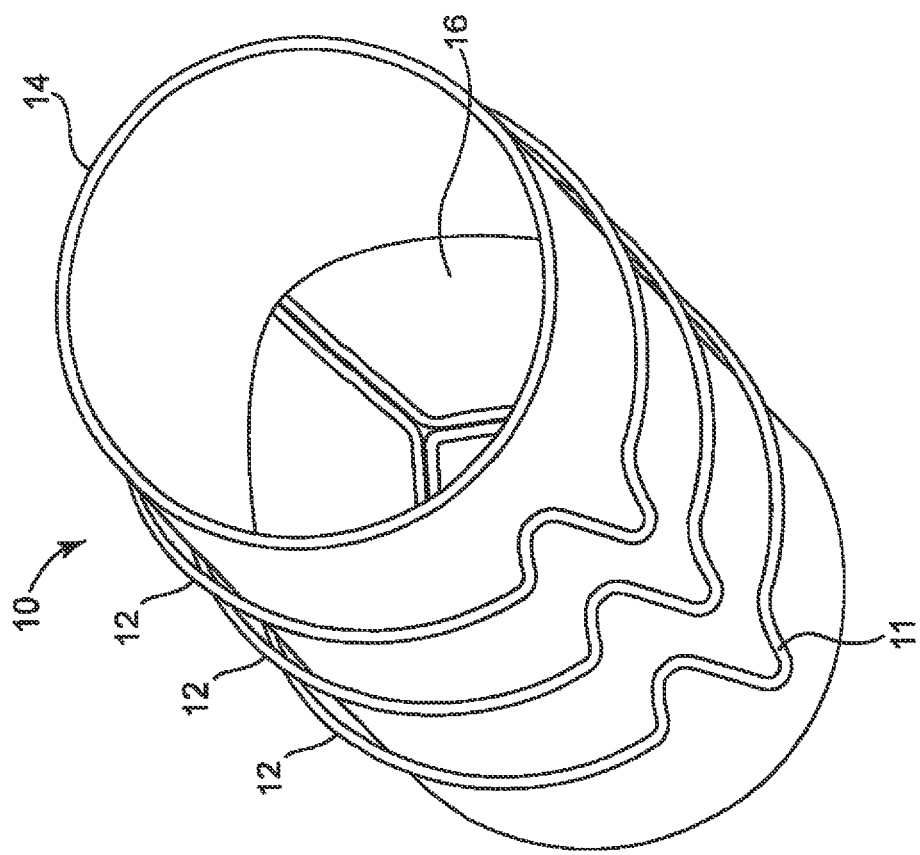
FIG. 1 is a perspective view of an expandable valved conduit in its relatively compressed state, according to one aspect of the invention.

FIG. 1 shows an assembly 10 comprising a plurality of circumferential support structures 12 and a valved conduit 14. The valved conduit 14 may comprise any suitable implantable valve conduit such as those utilizing bovine, equine, human, or porcine tissue, or other materials, such as polymeric and/or metallic materials. The conduit 14 may comprise an outer tubular structure within which multiple leaflets 16 are positioned. For example, the component of the valved conduit may comprise the Medtronic Freestyle (or Contegra) Implantable Valved Conduit, which is commercially available from Medtronic, Inc. of Minneapolis, Minn. However, it is also possible with the various embodiments of the invention that a valve having a single leaflet or moveable component is utilized within a valve conduit or other valve structure, including tissue valves or mechanical valves.

The support structures 12 may be attached to the outside surface of the outer tubular structure of the valved conduit 14 using conventional means, such as sutures, clips, adhesives, molding, weaving, and the like. Alternatively, the support structures 12 can be attached inside or be positioned within the conduit 14, such as can be accomplished with a molded elastomer or woven fabric.

The support structures 12 described herein can comprise a series of synthetic elements, mesh wires or wire segments. They can be independent or connected to each other via a link that can be permanent or temporary. The support structures 12 may be constructed from a number of suitable biocompatible materials such as polyester, materials such as the membrane "Gore-Tex", which is commercially available from W.L. Gore & Associates, Inc. of Elkton, Md., stainless steel, titanium, cobalt chromium alloy, platinum iridium, or other natural or man-made materials. Each support structure 12 may be unitary or homologous in composition or could comprise different segments made of different materials. The portion of each support structure 12 that allows or provides for its expansion may comprise a different geometry than the remaining portion of that support structure 12, or it may comprise a more malleable or deflectable portion. Each support structure 12 of a particular assembly 10 may be identical or similar to at least one other support structure 12 of that same assembly 10, or each support structure 12 of an assembly 10 may be different from the other support structures 12 of the assembly 10 in size, shape, material, and/or other characteristics. In one embodiment of an assembly 10 of the invention, all of the support structures 12 are identical in size, shape and composition. The support structures 12 will desirably be designed to provide sufficient support to hold the conduit diameter to a reasonably constant diameter, thereby enabling proper function and durability of the valve. Any number of configurations or structures can be used, such as those that can be laser cut, knitted, braided, or woven, for example. In addition, the support structures 12 will desirably be able to support the valve for changes in diameter at a minimum number of commissures and inflow regions of the valve. It is further desirable that the support structures are visible or detectable when using common medical imaging techniques, such as fluoroscopy, echocardiography, magnetic resonance imagery, and the like.

The elements of the support structures in other embodiments can alternatively be formed from a shape memory material such as nickel titanium alloy (e.g., Nitinol). With this material, the support structure is self-expandable from a contracted state to an expanded state, such as by the application of heat, energy, and the like, or by the removal of external forces (e.g., compressive forces).

Figure 2:
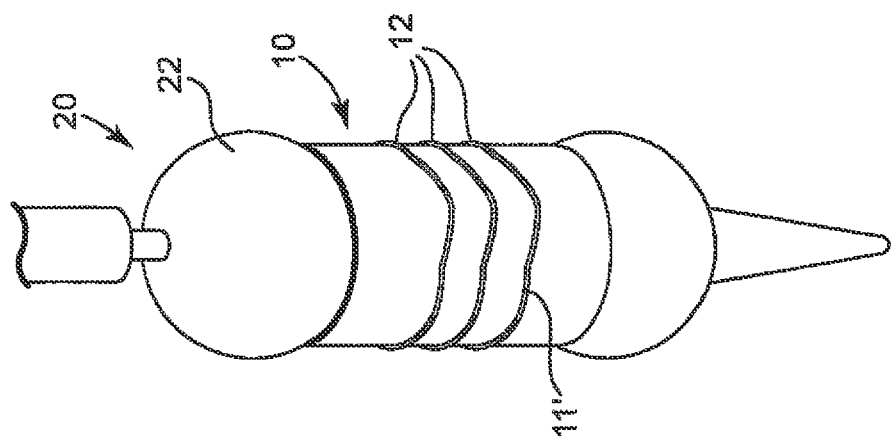
FIG. 2 is a perspective view of the expandable valved conduit of FIG. 1 in its relatively expanded state, along with a balloon expandable member positioned within the conduit.

The support structures 12 are adapted to be implanted in a patient in the generally cylindrical shape shown in FIG. 1, although the support structures 12 may instead have an outer shape that is oval, elliptical, irregular, or another shape that is chosen to be appropriate for the location in the patient where it will be implanted. The assembly 10 is configured so that it can be altered at any time after it is initially implanted within a patient. For example, the assembly 10 can be expanded immediately after a procedure of suturing the assembly 10 to the patient's anatomy in order to maximize the size of the orifice in which it is implanted. Alternatively, the assembly 10 could be expanded at some period of time after the initial implantation procedure, such as at the end of the useful life of the tissue of the valved conduit 14 or upon growth of the patient. In another embodiment, a first assembly 10 is implanted in a patient using an initial implantation procedure, then after some period of time (e.g., several months or years), a second procedure may be performed to expand the support structures 12 to the configuration of FIG. 2. This expanded configuration can then receive a second or replacement assembly 10 within its interior structure, if desired.

In one embodiment, the support structures 12 should be sufficiently strong to withstand the foreseeable stresses that may be encountered at the implantation site after the assembly 10 is implanted without any undesirable degradation that would result in conduit rupture and/or valve failure. However, the support structure 12 may be designed so that it will deflect in vivo from the configuration shown in FIG. 1 to that shown in FIG. 2 under the influence of a force that can be provided by an expandable assembly 20, for example. Expandable assembly 20 comprises an expandable balloon member 22. The balloon member 22 can be a high pressure, non-compliant balloon, such as a Numed Z-Med or Mullins valvuloplasty balloon, for example, although a wide variety of other types and manufacturers of balloons can be used. The balloon member 22 can be sized to produce a desired expansion of the support structure 12. The balloon member could be provided with various sizes and/or shapes to produce conduits of various sizes and/or shapes. The structure of the balloon member can be capable of expanding by various degrees and/or amounts within a prescribed range in order to provide for proper valve function. In one embodiment of the invention, the support structures 12 expand by deflection of the portions 11 from the configuration in FIG. 1, to the configuration 11' in FIG. 2. In this case, the entire conduit is uniformly expanded via expansion of the assembly 20.

In another embodiment, the expandable assembly 20 includes an expansion member that is not a balloon, but is a system having other components that can exert radial forces on the support structures so that they can be expanded to a larger diameter. For example, the expandable assembly may include a self-expanding stent that is capable of being compressed, positioned within the interior area of the support structures, and then released within the support structures. The self-expanding stent is designed so that it can thereby exert sufficient outward radial force when positioned within the support structures to diametrically deform and/or expand the support structures, in accordance with the various embodiments of the invention.

An alternative embodiment of a conduit 30 is illustrated in FIGS. 23 and 24. Conduit 30 includes a central area 32 that is at least slightly smaller in diameter than the end portions 34, 35 when the conduit is initially implanted. This central area 32 is the portion of conduit 30 in which valve leaflets can be positioned. Expandable support structures 36 are longitudinally spaced from each other in the central area 32, where the structures 36 are in their relatively expanded condition in FIG. 23 and in their relatively expanded condition in FIG. 24. An expansion mechanism (e.g., balloon) can be used to expand the central area 32 to a diameter that is closer to that of the end portions 34, 35, thereby making the conduit 30 more cylindrical in shape.

FIGS. 3 through 7 disclose an expandable support structure component 42 of the invention, as positioned relative to a stent or valve structure 40. Valve structure 40 includes a sewing ring 46 attached to three stent posts or commissural members 45. It is noted that this structure would be provided for a tricuspid valve, but that only two of such commissural members would be provided for a bicuspid valve, in another embodiment. All or a portion of the valve structure 40, including the sewing ring 46 and commissural members 45, can be covered by a flexible covering, which may be a tissue, polymer, fabric, metal, or cloth material to which leaflets (not shown) of the heart valve can be sewn. Further, as is known in the art, the internal structure of each of the commissural members 45 can be formed of a stiff but resiliently bendable material. This construction allows the commissural members 45 to be deflected by the application of an external or internal radial force.

The valve structure 40 is generally tubular in shape, defining an internal area that extends from an inflow end to an outflow end. Alternatively, the shape of the valve structure can be oval, elliptical, irregular, or any other desired shape. The internal area is essentially composed of the valve structure 40, and the valve structure 40 selectively allows for fluid flow into or out of the lumen of the natural heart valve in which it is implanted. Thus, the internal area is alternatively open and closed to the lumen of the natural heart valve in which it is inserted via movement of leaflets. For ease of illustration, leaflets associated with valve structure 40 are not shown in FIGS. 4 and 5.

As referred to herein, the prosthetic heart valves (e.g., valves that utilize a valve structure 40) used in accordance with the devices and methods of the invention may include a wide variety of different configurations, such as a prosthetic heart valve having one or more tissue leaflets, a synthetic heart valve having polymeric leaflets, or a mechanical valve, and can be specifically configured for replacing any heart valve. That is, the prosthetic heart valves of the invention can generally be used for replacement of aortic, mitral, tricuspid, or pulmonic valves, for use as a venous valve, or to replace a failed bioprosthesis, such as in the area of an aortic valve or mitral valve, for example. The replacement prosthetic heart valves of the invention can be employed to functionally replace stentless bioprosthetic heart valves as well.

The support structure 42 is part of the valve structure 40 and includes portions that generally follow the shape of the stent posts 45. Arch or member 44 of the support structure 42 can be deformed or modified after the valve structure 40 has been implanted to effectively enlarge the size of the orifice of the valve structure 40. In an initial implanted configuration, the support structure 42 may comprise the shape shown in FIGS. 3-4 and 7. In a subsequent procedure (which could potentially be any period of time later, such as minutes, hours, days, months or years), the shape of the support structure 42 can be modified such that member 44 shown in FIGS. 3 and 4 assumes the shape shown as member 44' in FIGS. 5 and 6. In this way, the internal area or diameter of the support structure 42 will be larger in order to provide the maximum available orifice area based on the patient's anatomy. In addition, expansion of the support structure 42 can put the valve structure in closer contact with the vessel anatomy, thereby improving the paravalvular seal, which can thereby reduce the degree of paravalvular leakage. Expansion of the support structure can also improve the stability of the surgical valve implant, which can reduce the chances for dehiscence. It is contemplated that an intermediate deformation of the member 44 can also occur so that the internal area has a size that is between that shown in FIGS. 4 and 5. It should be noted that the shape of member 44 shown in FIGS. 3-7 are not intended to be limiting. Any suitable shapes or mechanisms may be utilized that allow for expansion of the valve support structure 42, such as sinusoidal, accordion, triangular or any combination of segments and/or arcuate shapes.

Figure 4:
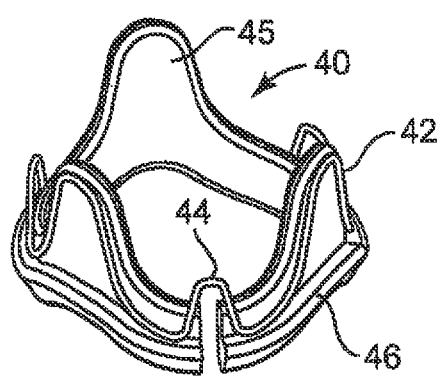
FIG. 4 is a perspective view of the stent of FIG. 3 assembled to additional components of a valve assembly, with the stent in a first implantable configuration. The fabric covering is removed from the frame of the valve assembly in the area of an expansion joint for illustration purposes.
Figure 5:
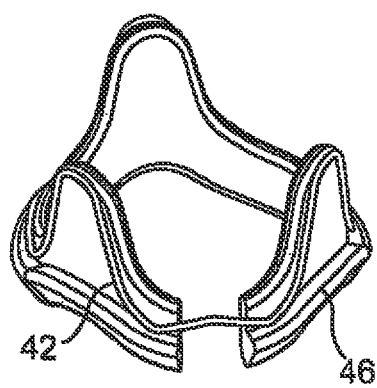
FIG. 5 is a perspective view of the assembly of FIG. 4 with the stent or member or frame expanded from the first implantable configuration to a second implantable configuration.
Figure 7:
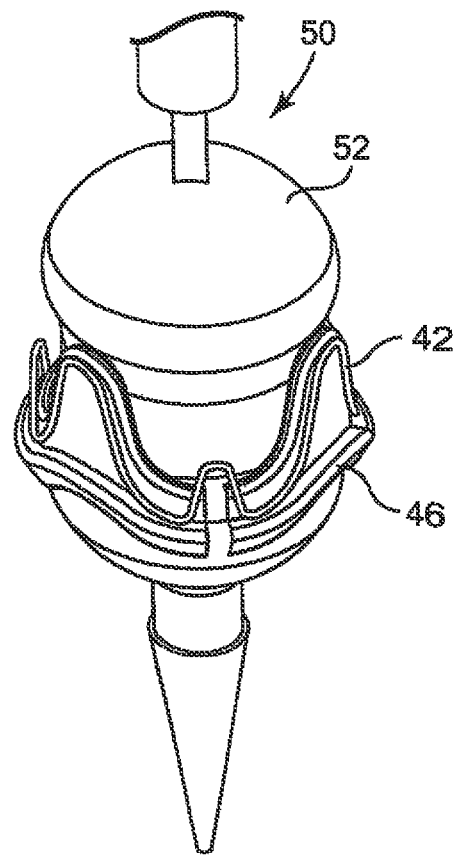
FIG. 7 is a perspective view of a balloon expandable member positioned within a valve assembly that is configured as is generally shown in FIGS. 3 and 4.

It is noted that the gap in the sewing ring 46 shown in FIGS. 4, 5, and 7, for example, is provided in the Figures for illustrative purposes. Such a gap would not typically be provided, although it is contemplated that such sewing ring 46 does include such a gap. When the base portion of the sewing ring 46 includes such a gap, cloth or another material that is used to cover the rest of the sewing ring 46 would preferably span such a gap to provide a continuous cover around the perimeter of the sewing ring 46. In this way, the paravalvular seal can be maintained more easily once the device is implanted in a patient. This material may be stretchable or otherwise deformable to allow for expansion of the overall size of the valve, if desired. If the sewing ring 46 does not include a gap, the ring 46 can be expandable or deformable, such as can be accomplished with a deformable material (e.g., stretchable portions) and/or with one or more expandable portions.

Figure 3:
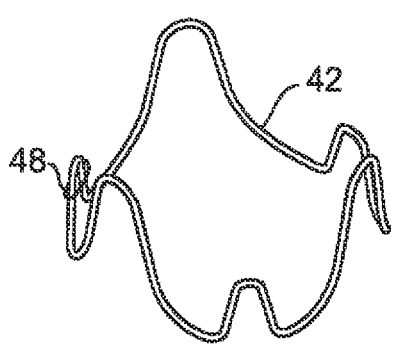
FIG. 3 is a perspective view of an expandable stent or member or frame for a stented valve in its relatively compressed state, according to another aspect of the invention.
Figure 6:
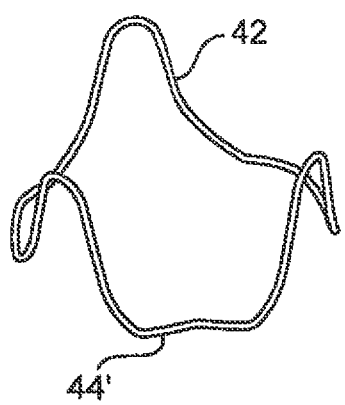
FIG. 6 is a perspective view of the stent or member or frame of FIG. 5.

FIG. 3 further illustrates an optional restraining element 48 that is positioned around a portion of one of the members 44. In this embodiment, support structure 42 can be a self-expanding component, where element 48 is positioned in such a way that it maintains the member 44 in an initial or unexpanded condition. The restraining element 48 can later be removed, deformed, or broken in order to allow the member 44 to deform or straighten, thereby allowing overall support structure 42 to expand to a larger diameter. One or more restraining elements 48 can be positioned relative to some or all of the members 44, wherein if more than one restraining element is used, the number of elements 48 that are deformed or removed can be chosen to allow the desired amount of expansion of the support structure 42. That is, only one element 48 may be removed in a first procedure to allow a first amount of expansion of the support structure 42, and then one or more additional elements 48 can be removed in one or more subsequent procedures to allow additional expansion of the support structure 42.

The valve support structure can also be composed of multiple elements that function together in a similar manner as a single valve support structure of the type previously described. For one example, the valve support structure may include an outer tubular structural piece having a central opening into which a connector can be positioned. Such a connector can be slideable relative to the outer tubular structural piece to allow for expansion of the outer periphery of the support structure. In another embodiment, tracks or rails can be used to allow for enlargement or expansion of the outer perimeter of the support structure.

A portion of a post-implant expansion system 50 is illustrated in FIG. 7, which comprises an expandable member 52 (e.g., a balloon that can be made of nylon, polyurethane, polyethylene, or polyethylene terephthalate (PET)). The system 50 may be utilized to modify the valve structure 40 from its first, unexpanded or partially expanded position to its second, expanded or partially expanded position. When the assembly 10 and valve structure 40 are in their second, expanded positions or configurations, they may be configured to receive a replacement transcatheter valve assembly. For example, a replacement valve conduit may be placed between the balloon 22 and the inside of the expandable conduit 14 in FIG. 2. In this embodiment, the assembly 10 is enlarged to its expanded condition and a replacement valve can be subsequently or simultaneously implanted therein. The native or existing valve can serve as a landing zone for a new heart valve implant. It is also possible to first expand the valve structure and to later insert a replacement transcatheter valve, where this can be performed either a relatively short time or a relatively long time after that expansion is performed.

FIGS. 8 and 9 illustrate another conduit configuration that can be used with certain aspects of the invention. In particular, a conduit 60 is illustrated in FIG. 8, which may comprise a specially designed expandable structure 62. This conduit 60 may or may not include a valve, depending on the application. In the depicted embodiment, the structure 62 comprises a mesh or woven type of material configuration (e.g., biocompatible polymer, metal, or combination thereof). The expandable structure 62 may comprise multiple members 66 disposed between adjacent elongated member 68, shown in FIG. 9, which can withstand stresses and tension during expected use of the heart valve assembly. However, the members 66 are designed to permanently deform, stretch, and/or break under the applied load of an expandable balloon member (not shown in FIGS. 8 and 9) or another device that imparts radial force. These members 66 may be fabric fibers, wires, or polymer elements, for example, which can break or stretch when placed under stress. If the members 66 stretch, such a stretching will preferably cause permanent or semi-permanent deformation of the members 66 so that they do not contract all the way back to their original size once the stress or load is removed. Members 64 are longer than members 66 and are curved or bent when the conduit 60 is in its relatively unexpanded condition. In addition, members 64 are more robust and are designed to withstand more stress than members 66. As a result, when a balloon or other expandable member is placed within the structure 62 and expanded, the members 66 will break or stretch and the members 64 will become straighter, thereby affording expansion of the expandable conduit 60. Members 66 can be differently configured at various portions of the conduit (e.g., inflow, outflow, etc.) to allow various shapes upon application of loads.

FIGS. 10-12 schematically illustrate a surgical method according to the invention. Specifically, FIG. 10 shows an aortic annulus 102, which may be relatively small, either due to the patient's natural anatomy or excessive calcification. An implantable valve 100 according to the invention is implanted in the patient's vasculature 104 (e.g., encompassing the native valve or occupying the position of a removed valve). Prior to this step, a sizing balloon or surgical valve sizer can be utilized to identify a desired maximum size of the valve 100.

A valve can be relative easily sewn into the patient's anatomy in the condition illustrated in FIG. 10. FIG. 11 then shows the use of a balloon 110 to expand the valve 100 to a larger circumference, which can be performed at any time after the initial valve implantation. FIG. 12 shows the valve 100' after it has been enlarged to an expanded condition. In this manner, the present invention can be utilized to maximize the effective valve orifice for a particular patient following the initial implantation procedure.

In another surgical embodiment, an expandable bioprosthetic valve may be implanted in the patient in an unexpanded, yet functional condition. That valve may be used until the useful life of its components reach an endpoint or the patient outgrows it. In this embodiment, an expandable member may then be utilized to modify or enlarge the valve to its expanded condition, and then a replacement transcatheter valve (which may itself be expandable) may be implanted with the first bioprosthetic valve. In this way, larger orifice areas following transcatheter valve procedures may be available than would be available with conventional surgical valves.

Figure 13:
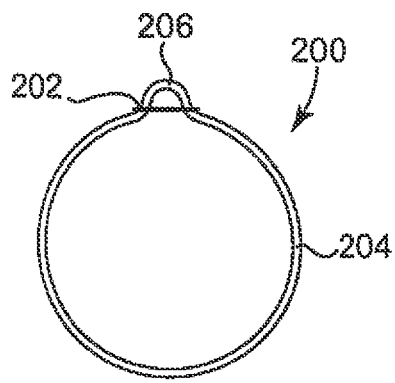
FIG. 13 is a top view of an expandable tubular component according to another aspect of the invention.
Figure 14:
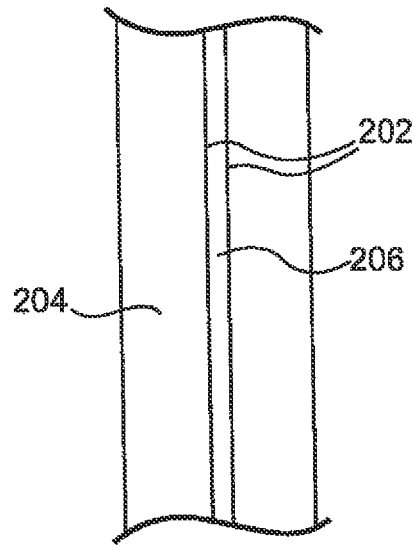
FIG. 14 is a side view of a portion of the component of FIG. 13.
Figure 15:
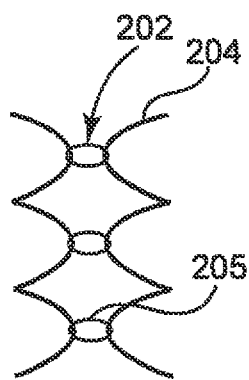
FIG. 15 is an enlarged side view of a portion of FIG. 14.

FIGS. 13-15 illustrate another embodiment of a component 200 of the invention. The component 200 comprises a tubular conduit 204 with at least two releasable seams 202, although it is possible that component 200 comprises more or less than two seams. The releasable seams 202 are positioned to essentially create a loop 206 of material from a tubular structure, where the seam 202 is sewn or otherwise secured (e.g., clips, sutures, and the like) along a seam line. When desired, the conduit 204 can be loaded radially, thereby breaking, deforming, stretching, or otherwise releasing material of the seams 202 (i.e., the loop 206) and allowing the component 200 to expand. That is, all or most of the material that makes up the loop 206 will be exposed to the inner area of the conduit 204 after expansion of the component 200. As shown in FIG. 15, the seam 202 may be created with a series of breakable or stretchable fibers (e.g., fabric fibers, wires, or polymeric elements), or discrete deformable elements 205 that can be broken or deformed by the application of a radial force, such as by a balloon expandable member. Although the loop 206 is shown on the exterior of the component 200 in FIG. 13, it may alternatively be placed within the interior area of the component 200.

Figure 16:
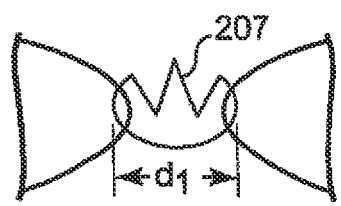
FIG. 16 is another embodiment of a side view of an expandable seam of the invention, with the seam in a relatively unexpanded condition.
Figure 17:
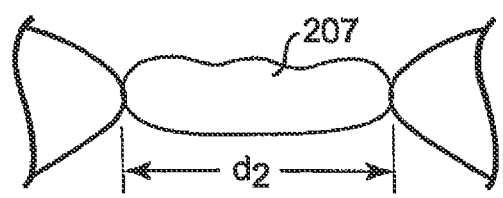
FIG. 17 is a side view of the seam of FIG. 16 in a relatively expanded condition.

FIGS. 16 and 17 illustrate a portion of another embodiment of a seam of a tubular conduit, which includes a series of discrete deformable elements 207, one of which is illustrated in these figures. Element 207 is shown in its unexpanded condition in FIG. 16 as having a diameter or dimension d1, then in its expanded condition in FIG. 17 as having a diameter or dimension d2. Diameter d1 is at least somewhat smaller than the diameter d2, which thereby illustrates the expansion in the seam area of the conduit. This deformation of the element 207 is preferably permanent or semi-permanent after the force that was used to deform the element is removed. Similarly, FIGS. 21 and 22 illustrate another deformable element 214. Element 214 is shown in its unexpanded condition in FIG. 21 as having a width or length d1, then in its expanded condition in FIG. 22 as having a width or length d2. Dimension d1 is smaller than the dimension d2, which again illustrates the expansion of the seam area of the conduit.

FIGS. 18-20 illustrate a portion of another embodiment of a loop 206 of a conduit seam, and further including a deformable element 208. Deformable element 208 includes lobes 212 and a bar 210 extending from each lobe 212. The lobes 212 are spaced from each other around the element 208. As is best illustrated in FIG. 19, material of the conduit 204 is looped relative to the bars 210 to create the loop of a seam. Application of radial force, such as the expansion of an internally positioned balloon, can deform the element 208, thereby allowing expansion of the seam.

The present invention has now been described with reference to several embodiments thereof. The entire disclosure of any patent or patent application identified herein is hereby incorporated by reference. The foregoing detailed description and examples have been given for clarity of understanding only. No unnecessary limitations are to be understood therefrom. It will be apparent to those skilled in the art that many changes can be made in the embodiments described without departing from the scope of the invention. Thus, the scope of the present invention should not be limited to the structures described herein, but only by the structures described by the language of the claims and the equivalents of those structures.

What is claimed is:

1. A prosthetic heart valve comprising:
a valved conduit comprising:
a generally tubular structure comprising a proximal end, a distal end, and a central portion between the proximal and distal ends, wherein a length of the tubular structure adjacent to at least one of the proximal and distal ends has a larger diameter in its unexpanded condition than a diameter of the central portion in its unexpanded condition; and
at least one leaflet attached within an interior area of the tubular structure in the central portion;
a plurality of support structures spaced from each other and attached to the central portion of the tubular structure, wherein each of the support structures is expandable from a first configuration to a second configuration when subjected to internal radial stress, wherein the internal area of each support structure is smaller in its first configuration than in its second configuration, and wherein at least one of the plurality of support structures extends continuously about an entire circumference of the tubular structure.

2. The heart valve of claim 1, wherein each of the support structures is attached to an outer surface of the central portion of the tubular structure.

3. The heart valve of claim 1, wherein each of the support structures is attached to an inner surface of the central portion of the tubular structure.

4. The heart valve of claim 1, wherein each of the support structures is embedded within an outer wall of the central portion of the tubular structure.

5. The heart valve of claim 1, wherein the heart valve is surgically implantable in a patient with the support structures in their first configuration, and wherein the support structures are expandable to their second configuration in response to the application of radial stress by a radial expansion system.

6. The heart valve of claim 1, wherein the first configuration of each of the support structures comprises a shaped portion, and wherein the shaped portion of each of the support structures is at least partially straightened when the support structure is in its second configuration.

7. The heart valve of claim 1, wherein the length of the tubular structure adjacent to the at least one of the proximal and distal ends has a consistent diameter in its unexpanded condition.

8. A prosthetic heart valve comprising a valved conduit comprising a generally tubular structure having at least one leaflet attached within its interior area, wherein the tubular structure comprises:
- a plurality of longitudinal support members spaced from each other around the perimeter of the tubular structure;
- at least one deformable member attached at a first end to a first longitudinal support member and at a second end to an adjacent second longitudinal support member, wherein the at least one deformable member is reconfigurable when the tubular structure is subjected to an internal radial stress.

9. The heart valve of claim 8, wherein the at least one deformable member is permanently deformable.

10. The heart valve of claim 8, wherein the at least one deformable member is breakable.

11. The heart valve of claim 8, wherein at least one of the deformable members has a first length in an unexpanded condition of the tubular structure and a second length in an expanded condition of the tubular structure, wherein the first length is smaller than the second length.

12. The heart valve of claim 11, wherein the first and second lengths of at least one of the deformable members corresponds to a distance between two adjacent longitudinal support members.

13. The heart valve of claim 8, further comprising at least one connector member attached at a first end to the first longitudinal member and at a second end to the second longitudinal member, wherein the at least one connector member has a higher strength than a strength of the at least one deformable member such that when the tubular structure is subjected to an internal radial stress, the at least one deformable member will deform by a sufficient amount that the distance between the first and second longitudinal support members will increase while the connector member remains attached to the first and second longitudinal support members.

* * * * *